(12) United States Patent
Alsalhi et al.

(10) Patent No.: US 10,059,601 B1
(45) Date of Patent: Aug. 28, 2018

(54) **SYNTHESIS OF SILVER NANOPARTICLES FROM *ABELMOSCHUS ESCULENTUS* EXTRACT**

(71) Applicant: KING SAUD UNIVERSITY, Riyadh (SA)

(72) Inventors: Mohamad Saleh Alsalhi, Riyadh (SA); Sandhanasamy Devanesan, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/730,653

(22) Filed: Oct. 11, 2017

(51) Int. Cl.
| | |
|---|---|
| *C01G 5/00* | (2006.01) |
| *B22F 9/24* | (2006.01) |
| *A61K 33/38* | (2006.01) |
| *A61K 36/18* | (2006.01) |
| *A61K 9/14* | (2006.01) |

(52) U.S. Cl.
CPC ............ *C01G 5/00* (2013.01); *A61K 9/148* (2013.01); *A61K 33/38* (2013.01); *A61K 36/18* (2013.01); *B22F 9/24* (2013.01); *A61K 2236/15* (2013.01); *A61K 2236/331* (2013.01); *A61K 2236/53* (2013.01); *C01P 2004/64* (2013.01)

(58) Field of Classification Search
CPC .......... C01G 5/00; A61K 9/148; A61K 36/18; A61K 33/38; A61K 2236/331; A61K 2236/15; A61K 2236/53; B22F 9/24; C01P 2004/64
See application file for complete search history.

(56) References Cited

U.S. PATENT DOCUMENTS

| | | | |
|---|---|---|---|
| 8,057,682 | B2 | 11/2011 | Hoag |
| 8,455,226 | B2 | 6/2013 | De Windt |
| 9,428,399 | B1 | 8/2016 | Awad |
| 2011/0110723 | A1 | 5/2011 | Varma |
| 2015/0024204 | A1 | 1/2015 | Amanchi Bala |

FOREIGN PATENT DOCUMENTS

CN         101912976         10/2010

OTHER PUBLICATIONS

Pande, N. et al., "Ecofriendly synthesis and applications of silver nanoparticles" Journal of Chemical and Pharmaceutical Research, 2014, 6(9):403-410.*

Jayaseelan, Chidambaram, et al. "Green synthesis of gold nanoparticles using seed aqueous extract of Abelmoschus esculentus and its antifungal activity." industrial crops and products 45 (2013): 423-429.*

(Continued)

*Primary Examiner* — Richard M Rump
(74) *Attorney, Agent, or Firm* — Richard C. Litman

(57) ABSTRACT

The synthesis of silver nanoparticles from plant extract includes providing a solution including silver nitrate; providing an aqueous extract of the *Abelmoschus esculentus* (Okra) plant or plant part; mixing the silver nitrate solution and the extract solution to form an aqueous mixture; and resting the aqueous mixture for a period of time to form silver nanoparticles (AgNPs). The resulting silver nanoparticles demonstrate antimicrobial activity against both gram-positive and gram-negative pathogens.

8 Claims, 5 Drawing Sheets

(56) References Cited

OTHER PUBLICATIONS

Banerjee et al., Leaf Extract Mediated Green Synthesis of Silver Nanoparticles from Widely Available Indian Plants: Synthesis, Characterization, Antimicrobial Property and Toxicity Analysis, Bioresources and Bioprocessing, 1 pp. 1-10 (2014).

Mollick et al., Studies on Green Synthesized Silver Nanoparticles using *Abelmoschus esculentus* (L.) Pulp Extract Having Anticancer (in vitro) and Antimicrobial Applications, Arabian J. of Chem. (2015).

\* cited by examiner

E. coli

P. aeruginosa

P. vulgaris

S. typhimurium

S. sonnei

B. subtilis

K. pneumoniae

S. aureus

S. epidermidis

S. pyogenes

SYNTHESIS OF SILVER NANOPARTICLES FROM *ABELMOSCHUS ESCULENTUS* EXTRACT

BACKGROUND OF THE INVENTION

1. Field of the Invention

The present invention relates to nanotechnology, and particularly to the synthesis of silver nanoparticles using *Abelmoschus esculentus* flower extract.

2. Description of the Related Art

An emerging field in nanotechnology is the synthesis of metal nanoparticles using herbal plants. Metal nanoparticles display improved and/or novel properties compared to their source materials. These properties may be derived from their size, morphology, or distribution. Silver nanoparticles are of particular interest because of their antimicrobial, anticancer, and cytotoxic activities.

Various chemical and mechanical methods of producing nanoparticles have been developed, including ball milling, thermal quenching, precipitation techniques, vapor deposition. However, these methods are often costly, and may result in toxic byproducts.

Biological approaches, including use of microorganisms or plant extracts to synthesize metal nanoparticles, have been suggested. However, synthesis of nanoparticles using microorganisms involves an expensive process requiring cell culture and multi-step purification.

Thus, an affordable method of biologically synthesizing antimicrobial silver nanoparticles solving the aforementioned problems is desired.

SUMMARY OF THE INVENTION

The synthesis of silver nanoparticles (AgNPs) from a plant extract includes providing a solution including silver nitrate; providing an aqueous extract of the *Abelmoschus esculentus* (Okra) plant or plant part; mixing the silver nitrate solution and the extract solution to form an aqueous mixture; and resting the aqueous mixture for a period of time to form silver nanoparticles (AgNPs). The AgNPs may be used as antimicrobial agents against gram positive and gram negative pathogens. The synthesis method is inexpensive, environmentally friendly, and produces silver nanoparticles with an average diameter of about 13.24 nm.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The synthesis of silver nanoparticles (AgNPs) from a plant extract includes providing a solution including silver nitrate; providing an aqueous extract of the *Abelmoschus esculentus* (Okra) plant or plant part; mixing the silver nitrate solution and the extract solution to form an aqueous mixture; and resting the aqueous mixture for a period of time to form a suspension including silver nanoparticles (AgNPs). Synthesis of the silver nanoparticles (AgNPs) can begin about 24, about 48, or about 72 hours after mixing. The resulting AgNPs can have a particle size ranging from about 5 nm to about 19 nm.

The suspension including the AgNPs may be used as antimicrobial agents. For example, the suspension including AgNPs can effectively inhibit or prevent growth of gram positive and gram negative bacteria. An effective amount of the suspension can be contacted with the pathogen or locus of the pathogen to prevent or inhibit growth thereof.

The extract can be a flower extract derived from Okra flowers. As used herein, the term "flower extract" includes, for example, any chemical or combination of chemicals found in the flower of the plant, as well as any derivatives of the chemicals or compounds found in the flower via extraction. The "flower extract" can be obtained from the plant by any process, including but not limited to cold water extraction, hot water extraction, or extraction using an organic solvent. The resulting AgNPs may be used as antimicrobial agents against gram positive and gram negative pathogens. The following examples will further illustrate the synthesis process.

Example 1

Synthesis of Silver Nanoparticles from Okra Flowers

AgNPs were synthesized by the following method. Fresh Okra flowers were collected from an organic agriculture farm house in the Riyadh region of the Kingdom of Saudi Arabia. About 250 grams of flower were taken and the flowers were dried at room temperature, producing dried Okra flowers. The dried Okra flowers were ground into a fine powder and then about 5 grams of powder was soaked in about 100 ml of double distilled water ($DH_2O$) for about 24 hours, producing aqueous Okra flower extract. The aqueous Okra flower extract was filtered using Whatman™ No. 1 filter paper, producing filtered, aqueous Okra flower extract. The filtered flower extract was dark black in color. About 1 mM silver nitrate ($AgNO_3$) was dissolved by mixing in about 250 ml of $DH_2O$, producing a silver nitrate solution. About 5 ml of the filtered Okra flower extract was added to the silver nitrate solution and mixed thoroughly, forming an aqueous mixed solution. The aqueous mixed solution was then rested at room temperature for up to about 72 hours. After about 72 hours, the aqueous mixed solution was observed to change from colorless to dark brown. This color change is visual evidence of formation of AgNps or reduction of silver ions into AgNPs.

Figure 1:
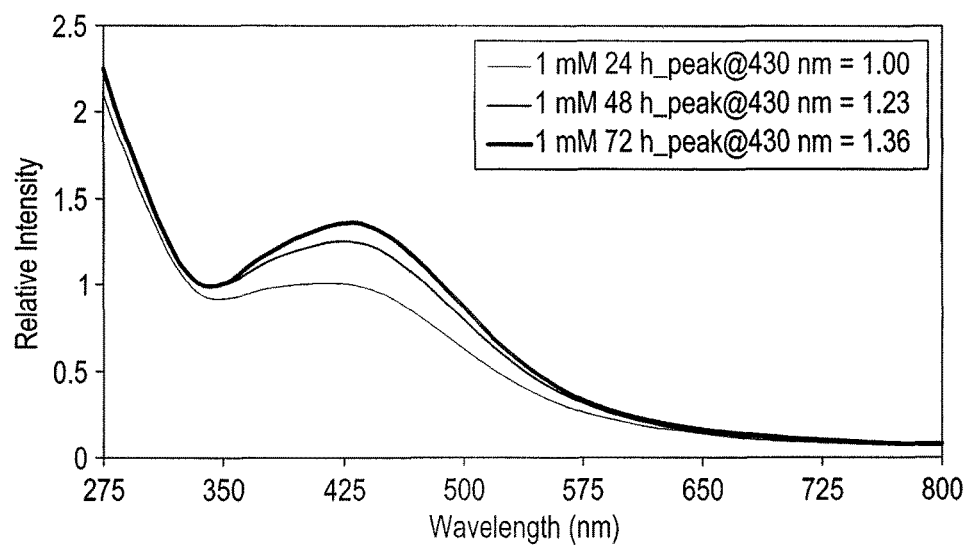
FIG. 1 is the Ultra-Violet Visible Spectroscopy (UV-Vis) spectrum of AgNPs synthesized from Okra flowers recorded after 24 hours, 48 hours, and 72 hours of reaction time according to the present invention.

The synthesis of Okra flower AgNPs was first confirmed by ultraviolet-visible spectroscopy. FIG. 1 shows the UV-Vis absorption spectrum for the Okra flower AgNPs synthesized in Example 1. The UV-Vis spectrum was monitored at time intervals for the final resting step of about 24 hours, about 48 hours, and about 72 hours. These time intervals correspond respectively to values of about 1.00, 1.23 and 1.36 at a peak wavelength of 430 nm.

Figure 2:
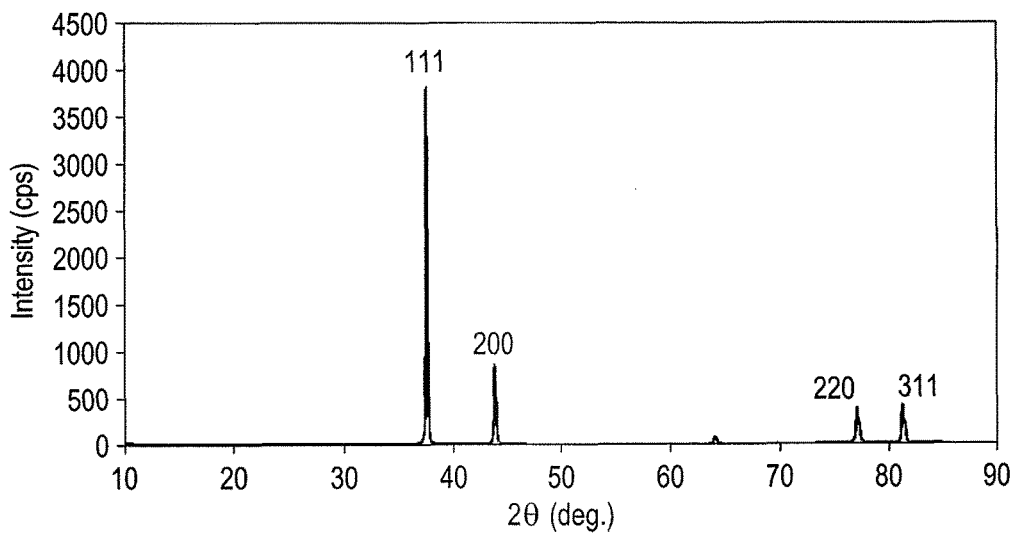
FIG. 2 is the X-Ray Diffraction (XRD) pattern of AgNPs synthesized from Okra flower extract according to the present invention.

The synthesis of AgNPs was next confirmed by X-ray diffraction. FIG. 2 shows the XRD spectrum of about 1 mM of Okra flower AgNPs. The spectrum has four distinct diffraction peaks at 38°, 44°, 77° and 84°, corresponding to intensity counts of 111, 200, 220 and 311, respectively. These results are consistent with the formation of AgNPs.

Figure 3:
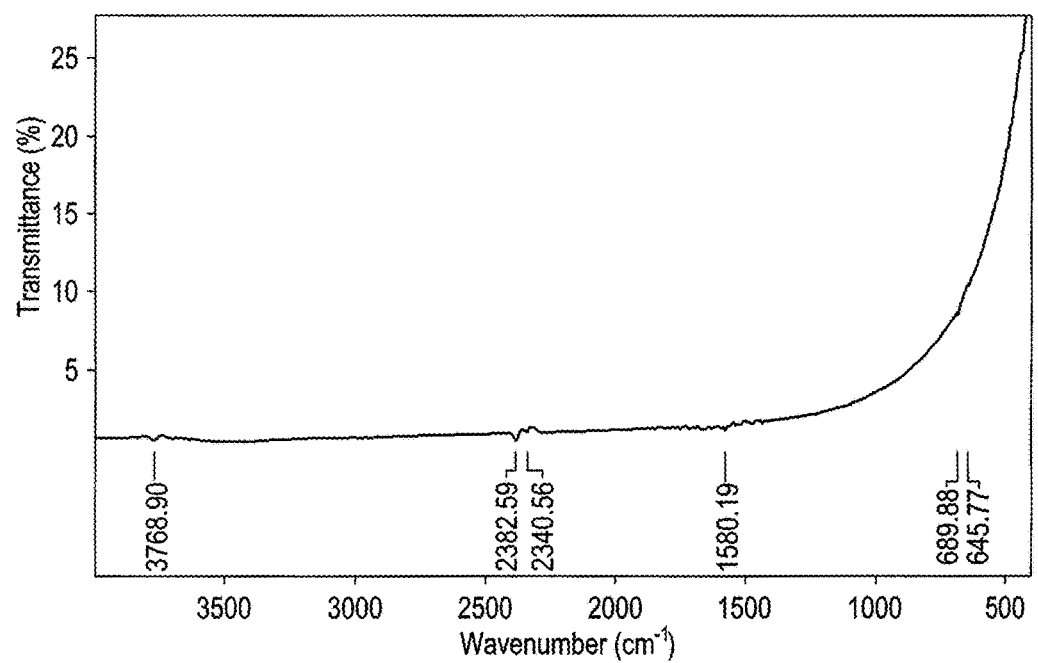
FIG. 3 is the Fourier Transform Infrared Spectroscopy (FTIR) spectra of AgNPs synthesized from Okra flower extract according to the present invention.

The AgNPs were also analyzed using FTIR. The FTIR spectrum obtained from Okra flower AgNPs is shown in FIG. 3. Four distinct peaks were observed at 3768.90, 2382, 1580.19 and 689.88 $cm^{-1}$. The band observed at 689.88 $cm^{-1}$ indicates the presence of AgNPs, according to this example.

Figure 4:
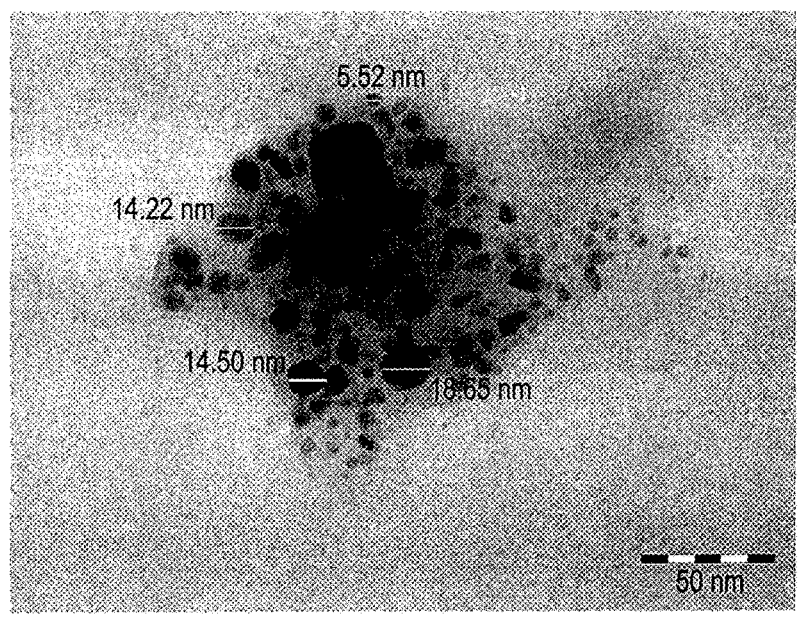
FIG. 4 is the Transmission Electron Microscopy (TEM) image of AgNPs synthesized from Okra flower extract according to the present invention.

FIG. 4 shows TEM images of the Okra flower AgNPs, demonstrating that the AgNPs have a spherical shape and range in diameter from about 5.52 nm to about 18.65 nm. The average particle diameter of the AgNPs according to this example is about 13.24 nm. As the biological activities of AgNPs are thought to depend upon the size of the particles, the small sizes of the Okra flower AgNPs synthesized according to this example suggests that they can possess enhanced antimicrobial activities against different gram positive and negative microorganisms.

Figure 5:
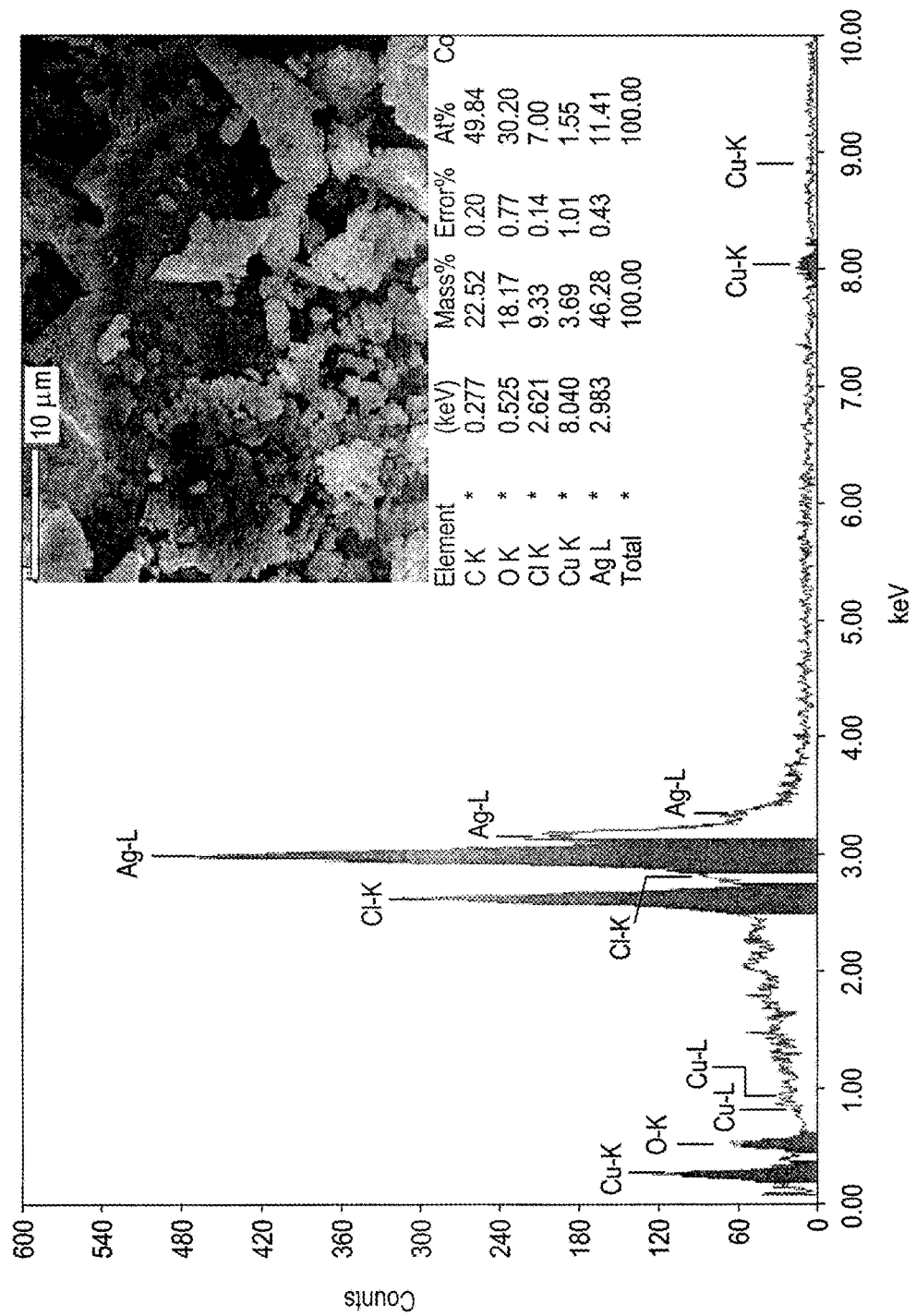
FIG. 5 is the Energy Dispersive X-Ray Spectroscopy (EDS) spectrum of AgNPs synthesized from Okra flower extract according to the present invention.
Figure 6A:
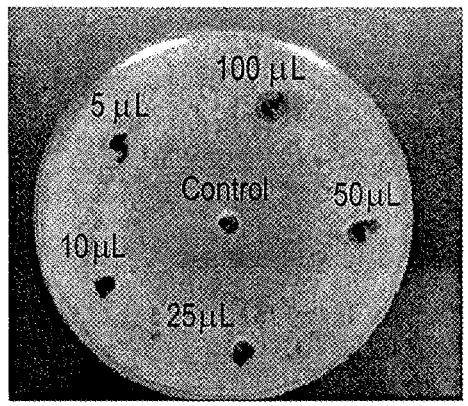
FIG. 6A is an analysis of the antimicrobial activity of 5 µl, 10 µl, 25 µl, 50 µl, and 100 µl of AgNPs synthesized from Okra flower extract against the gram negative bacterium *E. coli* according to the present invention.
Figure 6B:
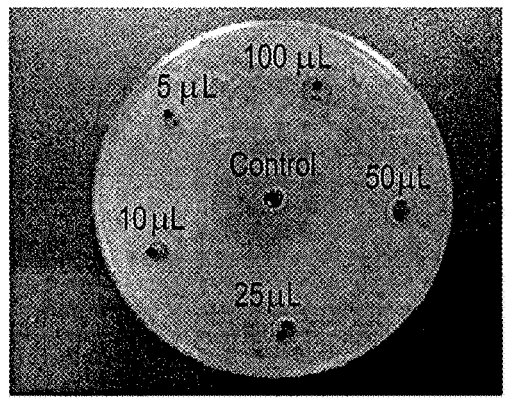
FIG. 6B is an analysis of the antimicrobial activity of 5 µl, 10 µl, 25 µl, 50 µl, and 100 µl of AgNPs synthesized from Okra flower extract against the gram negative bacterium *P. aeruginosa* according to the present invention.
Figure 6C:
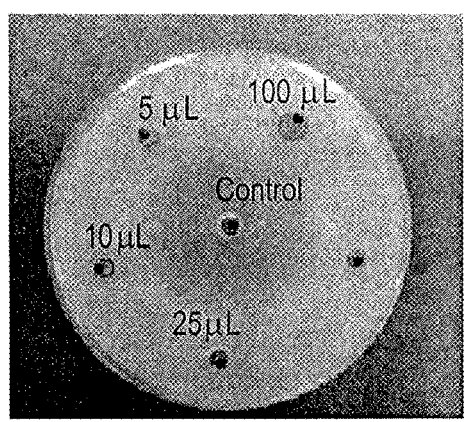
FIG. 6C is an analysis of the antimicrobial activity of 5 µl, 10 µl, 25 µl, 50 µl, and 100 µl of AgNPs synthesized from Okra flower extract against the gram negative bacterium *P. vulgaris* according to the present invention.
Figure 6D:
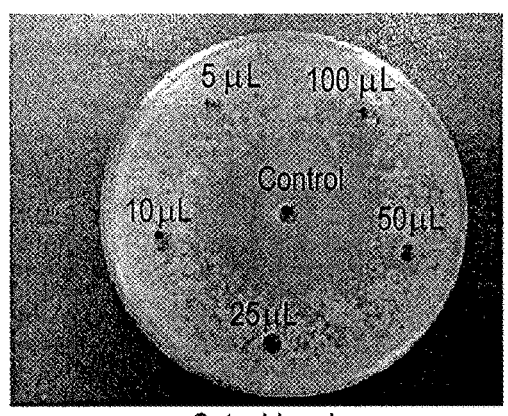
FIG. 6D is an analysis of the antimicrobial activity of 5 µl, 10 µl, 25 µl, 50 µl, and 100 µl of AgNPs synthesized from Okra flower extract against the gram negative bacterium *S. typhimurium* according to the present invention.
Figure 6E:
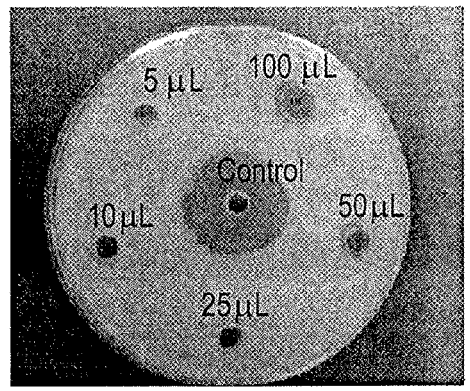
FIG. 6E is an analysis of the antimicrobial activity of 5 µl, 10 µl, 25 µl, 50 µl, and 100 µl of AgNPs synthesized from Okra flower extract against the gram negative bacterium *S. sonnei* according to the present invention.
Figure 7A:
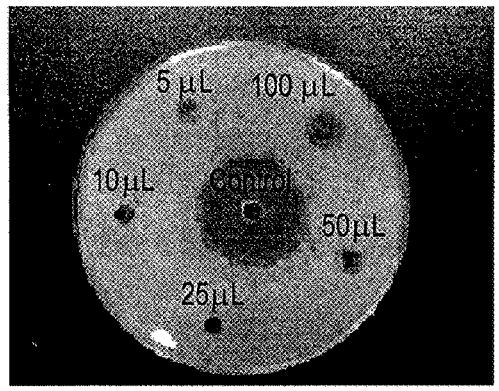
FIG. 7A is an analysis of the antimicrobial activity of 5 µl, 25 µl, 50 µl, and 100 µl of AgNPs synthesized from Okra flower extract against the gram positive bacterium *B. subtilis* according to the present invention.
Figure 7B:
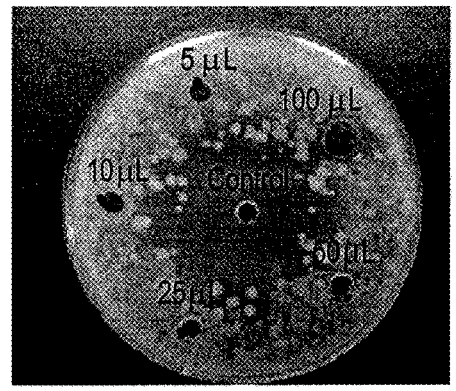
FIG. 7B is an analysis of the antimicrobial activity of 5 µl, 10 µl, 25 µl, 50 µl, and 100 µl of AgNPs synthesized from Okra flower extract against the gram positive bacterium *K. pneumoniae* according to the present invention.
Figure 7C:
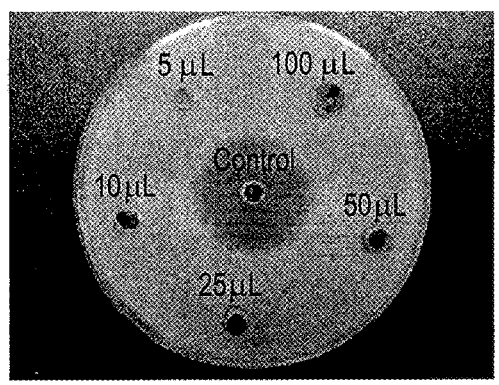
FIG. 7C is an analysis of the antimicrobial activity of 5 µl, 10 µl, 25 µl, 50 µl, and 100 µl of AgNPs synthesized from Okra flower extract against the gram positive bacterium *S. aureus* according to the present invention.
Figure 7D:
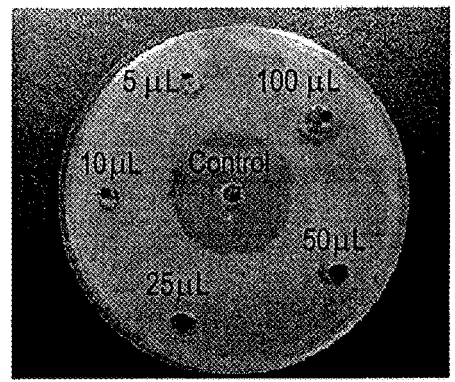
FIG. 7D is an analysis of the antimicrobial activity of 5 µl, 10 µl, 25 µl, 50 µl, and 100 µl of AgNPs synthesized from Okra flower extract against the gram positive bacterium *S. epidermidis* according to the present invention.
Figure 7E:
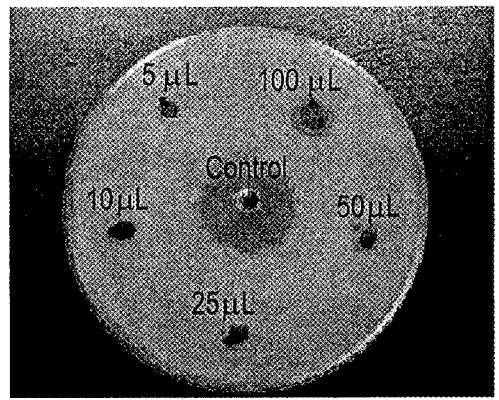
FIG. 7E is an analysis of the antimicrobial activity of 5 µl, 10 µl, 25 µl, 50 µl, and 100 µl of AgNPs synthesized from Okra flower extract against the gram positive bacterium *S. pyogenes* according to the present invention.

FIG. 5 shows an EDS spectrum, demonstrating the quantitative amount of different elements present in the Okra flower AgNPs. The EDS spectrum shows the presence of elements such as C K, O K, Cl K, Cu K, Ag L and their masses of 22.52, 18.17, 9.33, 3.69 and 46.28 respectively. EDS quantitative analysis demonstrated that the highest concentration of a single element in the Okra flower AgPs was silver, at about 46.28%.

Example 2

Establishing Antimicrobial Activity of Okra Flower AgNPs

Antimicrobial activity of Okra flower AgNPs was tested using the agar diffusion method. Standardized inoculums of about $1-2 \times 10^7$ colony forming units per milliliter with about 0.5 Mcfarl were prepared and introduced onto the surface of sterile agar plates. Sterile glass spreaders were used for even distribution of the inoculums. Five evenly spaced wells were created around the outer area of each plate, along with a central control well. Different concentrations (of about 5 μL, about 10 μL, about 25 μL, about 50 μL, and about 100 μL) of the Okra flower AgNPs were poured into individual wells. The antibiotic control used was 5 μg per mL Ciprofloxacin. The inhibition zones were measured in millimeters after about 24 hours of incubation at about 37 degrees Celsius. The antimicrobial activity of Okra flower AgNPs was assessed using gram negative pathogens *Escherichia coli* (ATCC 25922), *Pseudomonas aeruginosa* (ATCC 27584), *Proteus vulgaris* (ATCC 8427), *Salmonella typhimurium* (ATCC 14028) and *Shigella sonnei* (King Khalid Medical Hospital Riyadh), as shown in FIGS. 6A, 6B, 6C, 6D, and 6E, respectively. The antimicrobial activity was also assessed using gram positive pathogens *Bacillus subtilis* (MTCC 441), *Klebsiella pneumoniae* (G455), *Staphylococcus aureus* (ATCC 29213), *Staphylococcus epidermidis* (MTCC 3615) and *Streptococcus pyogenes* (ATCC 29213), as shown in FIGS. 7A, 7B, 7C, 7D, and 7E, respectively. The Okra flower AgNPs showed mild to strong activity increasing with concentration against the gram negative pathogens, except against *Proteus vulgaris*, and strong activity increasing with concentration against the gram positive pathogens, as seen in Table 1.

TABLE 1

Antimicrobial Activity of Okra Flower AgNPs Inhibition Zone Diameter (mm)

| Organism | 5 μL | 10 μL | 25 μL | 50 μL | 100 μL |
|---|---|---|---|---|---|
| *Escherichia coli* | — | — | — | 6 | 14 |
| *Pseudomonas aeruginosa* | — | — | — | 10 | 16 |
| *Proteus vulgaris* | — | — | — | — | — |
| *Salmonellatyphimurium* | — | — | 6 | 10 | 18 |
| *Shigella sonnei* | — | — | — | 6 | 12 |
| *Bacillus subtilis* | — | 6 | 7 | 8 | 12 |
| *Klebsiella pneumoniae* | — | — | — | 8 | 16 |
| *Staphylococcus aureus* | 6 | 7 | 9 | 10 | 12 |
| *Staphylococcus pidermidis* | — | 6 | 7 | 10 | 13 |
| *Streptococcus pyogenes* | — | — | 6 | 7 | 12 |

It is to be understood that the present invention is not limited to the embodiments described above, but encompasses any and all embodiments within the scope of the following claims.

We claim:

1. A method of synthesizing silver nanoparticles, comprising the steps of:
   providing a silver nitrate solution;
   providing an aqueous extract of *Abelmoschus esculentus*, wherein the aqueous extract of *Abelmoschus esculentus* is derived from dried flowers of *Abelmoschus esculentus*;
   mixing the silver nitrate solution with the aqueous extract of *Abelmoschus esculentus* to provide a mixture; and
   resting the mixture at room temperature for an amount of time to produce a suspension including the silver nanoparticles.

2. The method of synthesizing silver nanoparticles of claim 1, wherein said silver nitrate solution is prepared by dissolving about 1 mM silver nitrate in about 250 double distilled water.

3. The method of synthesizing silver nanoparticles of claim 1, wherein providing the aqueous extract comprises grinding said dried flowers of *Abelmoschus esculentus* into a fine powder and soaking the fine powder in water.

4. The method of synthesizing silver nanoparticles of claim 3, wherein about 5 grams of the fine powder is soaked in about 100 ml of double distilled water for about 24 hours to produce the extract solution.

5. The method of synthesizing silver nanoparticles of claim 4, further comprising the step of filtering the extract solution.

6. The method of synthesizing silver nanoparticles of claim 1, wherein the amount of time for the resting step is about 24 to about 72 hours.

7. The method of synthesizing silver nanoparticles of claim 6, wherein the amount of time for the resting step is about 72 hours.

8. A method of synthesizing silver nanoparticles, comprising the steps of:
   providing a silver nitrate solution;
   providing an aqueous extract of *Abelmoschus esculentus*, wherein the aqueous extract of *Abelmoschus esculentus* is derived from dried flowers of *Abelmoschus esculentus*;
   mixing the silver nitrate solution with the aqueous extract of *Abelmoschus esculentus* to provide a mixture; and
   resting the mixture at room temperature for an amount of time to produce a suspension including the silver nanoparticles, wherein the silver nanoparticles have an average diameter of about 13.24 nanometers.

\* \* \* \* \*